United States Patent
Murai et al.

(10) Patent No.: US 9,132,100 B2
(45) Date of Patent: Sep. 15, 2015

(54) PATCH CONTAINING NON-STEROIDAL ANTI-INFLAMMATORY DRUG

(71) Applicant: Reckitt Benckiser Healthcare International Limited, Berkshire (GB)

(72) Inventors: Naoki Murai, Toyama (JP); Seijiro Yama, Toyama (JP)

(73) Assignee: Reckitt Benckiser Healthcare International Limited, Slough, Berkshire (GB)

( * ) Notice: Subject to any disclaimer, the term of this patent is extended or adjusted under 35 U.S.C. 154(b) by 0 days.

(21) Appl. No.: 14/363,076

(22) PCT Filed: Dec. 4, 2012

(86) PCT No.: PCT/GB2012/053000
§ 371 (c)(1),
(2) Date: Jun. 5, 2014

(87) PCT Pub. No.: WO2013/083965
PCT Pub. Date: Jun. 13, 2013

(65) Prior Publication Data
US 2014/0335151 A1    Nov. 13, 2014

(30) Foreign Application Priority Data
Dec. 6, 2011  (GB) .................................. 1120908.7

(51) Int. Cl.
| A61K 9/70 | (2006.01) |
| A61K 47/10 | (2006.01) |
| A61K 47/32 | (2006.01) |
| A61K 31/192 | (2006.01) |

(52) U.S. Cl.
CPC .............. *A61K 9/7023* (2013.01); *A61K 9/7053* (2013.01); *A61K 9/7069* (2013.01); *A61K 9/7076* (2013.01); *A61K 31/192* (2013.01); *A61K 47/10* (2013.01); *A61K 47/32* (2013.01)

(58) Field of Classification Search
None
See application file for complete search history.

(56) References Cited

U.S. PATENT DOCUMENTS

2005/0129748 A1   6/2005   Takada et al.
2008/0299220 A1 * 12/2008  Tamarkin et al. ............. 424/600

FOREIGN PATENT DOCUMENTS

| EP | 1477164 A1 | 11/2004 |
| EP | 1611884 A1 | 1/2006 |
| WO | 2007049892 A1 | 5/2007 |
| WO | 2011081628 A1 | 7/2011 |

OTHER PUBLICATIONS

International Preliminary Report on Patentability dated Jun. 19, 2014.
International Search Report dated May 10, 2013.
Combined Search and Examination report dated Mar. 27, 2012 in related application GB1120908.7.
Biomaterials, vol. 14, No. 2, 1993, A. Apicella, et al., "Poly(ethyleneoxide) (PEO) and Different Molecular Weight PEO Blends Monolithic Devices for Drug Release," pp. 83-90.

* cited by examiner

*Primary Examiner* — Sue Liu
*Assistant Examiner* — Thor Nielsen
(74) *Attorney, Agent, or Firm* — Troutman Sanders LLP; Ryan A. Schneider; Elizabeth-Ann Weeks

(57) ABSTRACT

The present invention is directed to a patch containing a non-steroidal anti-inflammatory drug including an adhesive layer composed of a transdermal preparation on a support, the transdermal preparation including a) 10 to 40% by weight of a nonaqueous base material based on the total weight of the transdermal preparation, b) 1 to 10% by weight of a non-steroidal anti-inflammatory drug based on the total weight of the transdermal preparation, and c) a polyethylene glycol component composed of 0.3 to 5% by weight of a low molecular weight polyethylene glycol based on the total weight of the transdermal preparation, and 1 to 10% by weight of a high molecular weight polyethylene glycol based on the total weight of the transdermal preparation.

20 Claims, No Drawings

PATCH CONTAINING NON-STEROIDAL ANTI-INFLAMMATORY DRUG

CROSS-REFERENCE TO RELATED APPLICATIONS

This application is a U.S. National Stage of International Application No. PCT/GB2012/053000, filed 4 Dec. 2012, which claims the benefit of GB 1120908.7, filed 6 Dec. 2011, both herein fully incorporated by reference.

FIELD OF THE INVENTION

The present invention relates to patches containing a non-steroidal anti-inflammatory drug, and in particular relates to patches containing a non-steroidal anti-inflammatory drug, which include a transdermal preparation containing a polyethylene glycol component composed of a particular amount of a low molecular weight polyethylene glycol and a particular amount of a high molecular weight polyethylene glycol that can suppress crystallization or sublimation of the non-steroidal anti-inflammatory drug, of which an adhesive layer can be readily formed, and which have excellent skin permeability of the drug.

BACKGROUND OF THE INVENTION

General examples of common administration methods of pharmaceutical drugs include oral administrations, transdermal administrations through, for example, the skin, hair, and oral cavity (including the mucosa), and injections. Among them, a patch for the transdermal administration is a preferred administration method because it is unlikely to cause side effects of a pharmaceutical drug and it is readily administered. Transdermal patches for drug delivery are known from US 2005/0129748. Melt-extuded thin strips containing nicotine for oral administration are known from WO 2011/081628.

From such viewpoints, there is disclosed the development of the patches containing a non-steroidal anti-inflammatory drug for example Japanese Patent Application Publication No. JP-A-2002-193793, PCT Patent Application No. WO-A-1-2004/82672 and Japanese Patent Application No. JP-A-2006-045099.

Such a patch is commonly used as a preparation including a support on which an adhesive layer composed of an adhesive composition (ointment composition) is formed. The adhesive composition includes an "aqueous adhesive composition" using water-soluble polymers, and the like, and a "nonaqueous adhesive composition" using resins, and the like.

BRIEF SUMMARY OF THE INVENTION

Here, the "nonaqueous adhesive composition" has an advantage of capable of dissolving pharmaceutical drugs that are poorly soluble in water. Hence, the composition can be advantageously used as the adhesive composition for a patch containing a non-steroidal anti-inflammatory drug that is poorly soluble in water.

However, the "nonaqueous adhesive composition" to which the pharmaceutical drug is added can dissolve the non-steroidal anti-inflammatory drugs when it is prepared, but some of the non-steroidal anti-inflammatory drugs may be crystallized in the "nonaqueous adhesive composition" over time and the precipitated crystal may be sublimated. As a result, the transdermal absorbability of the drug may be reduced.

DETAILED DESCRIPTION

It is an object of the present invention to provide a patch containing a non-steroidal anti-inflammatory drug that can suppress crystallization or sublimation of the drug, whose adhesive layer is readily formed, and that has excellent skin permeability of the drug.

Conventionally, the crystallization of a non-steroidal anti-inflammatory drug in an adhesive layer can be suppressed by, for example, the increase in the amount added of polyethylene glycol (PEG 400) as a polyhydric alcohol. However, such an increase in the amount added of polyethylene glycol leads to a new problem that the adhesive layer obtains too high cohesiveness to interfere with the processing into a patch.

In order not to cause the problem, it has been considered that the amount added of the polyethylene glycol (PEG 400) should be suppressed to about 5% by weight.

The inventors of the present invention have carried out intensive studies in order to solve the problems above, and as a result, have found that the addition of a high molecular weight polyethylene glycol that is solid at an ordinary temperature, at a particular ratio in addition to a low molecular weight polyethylene glycol such as polyethylene glycol (PEG 400) as the polyethylene glycol component can suppress crystallization or sublimation of the non-steroidal anti-inflammatory drug and can maintain the flowability of an adhesive layer within an appropriate range to readily form the adhesive layer.

In addition, it have been also found that a patch formed with the resultant adhesive layer has an excellent skin permeability of a non-steroidal anti-inflammatory drug to be used, and the present invention has been accomplished.

According to the present invention there is provided a patch including an adhesive layer composed of a transdermal preparation on a support, the transdermal preparation including a) 10 to 40% by weight of a nonaqueous base material based on the total weight of the transdermal preparation, b) 1 to 10% by weight of a non-steroidal anti-inflammatory drug based on the total weight of the transdermal preparation, and c) a polyethylene glycol component composed of 0.3 to 5% by weight of a low molecular weight polyethylene glycol based on the total weight of the transdermal preparation, and 1 to 10% by weight of a high molecular weight polyethylene glycol based on the total weight of the transdermal preparation.

Typically, the content of the low molecular weight polyethylene glycol in the patch is 0.3 to 2% by weight based on the total weight of the transdermal preparation.

The non-steroidal anti-inflammatory drug is selected from a group consisting of ibuprofen, ketoprofen, flurbiprofen, diclofenac, and naproxen. Preferably the non-steroidal anti-inflammatory drug is selected from a group consisting of ibuprofen, ketoprofen, and naproxen. More preferably the non-steroidal anti-inflammatory drug is ibuprofen. Typically the content of the ibuprofen is 2.5 to 10% by weight based on the total weight of the transdermal preparation.

Preferably the nonaqueous base material of the patch can be composed of a styrene-isoprene-styrene block copolymer (SIS) and polyisobutylene.

According to the present invention, a patch containing a non-steroidal anti-inflammatory drug that can suppress crystallization or sublimation of the drug, of which an adhesive layer is readily formed, and that has excellent skin permeability of the drug can be provided.

The patch containing a non-steroidal anti-inflammatory drug of the present invention has excellent storage stability, and thus the amount of a non-steroidal anti-inflammatory drug contained in the preparation changes minimally from the start of storage even when it is stored for a long time.

The patch containing a non-steroidal anti-inflammatory drug of the present invention has an advantage of not causing a rash due to a remaining plaster or adhesive because the patch can be completely removed without remaining the plaster or adhesive on an affected area.

The patch containing a non-steroidal anti-inflammatory drug of the present invention is a patch that includes an adhesive layer composed of a transdermal preparation on a support.

The transdermal preparation is characterized by including
a) 10 to 40% by weight of a nonaqueous base material based on the total weight of the transdermal preparation,
b) 1 to 10% by weight of a non-steroidal anti-inflammatory drug based on the total weight of the transdermal preparation, and
c) a polyethylene glycol component composed of
0.3 to 5% by weight of a low molecular weight polyethylene glycol based on the total weight of the transdermal preparation and
1 to 10% by weight of a high molecular weight polyethylene glycol based on the total weight of the transdermal preparation.

Specific examples of the non-steroidal anti-inflammatory drug capable of being included in the transdermal preparation include ibuprofen, ketoprofen, flurbiprofen, diclofenac, and naproxen.

Among them, ibuprofen, ketoprofen, and naproxen are preferred and ibuprofen is more preferred.

The amount used of the non-steroidal anti-inflammatory drug ranges from 1 to 10% by weight based on the total weight of the transdermal preparation, preferably ranging from 2.5 to 10% by weight based on the total weight of the transdermal preparation, and more preferably ranging from 5 to 10% by weight based on the total weight of the transdermal preparation.

It is preferable to use ibuprofen as the non-steroidal anti-inflammatory drug in a range from 2.5 to 10% by weight based on the total weight of the transdermal preparation, and it is more preferable to use ibuprofen in a range from 5 to 10% by weight based on the total weight of the transdermal preparation.

The polyethylene glycol component capable of being included in the transdermal preparation is composed of a low molecular weight polyethylene glycol, and a high molecular weight polyethylene glycol.

Examples of the low molecular weight polyethylene glycol include a polyethylene glycol that is liquid at an ordinary temperature (25° C.), such as polyethylene glycols having an average molecular weight of about 200 to 600, and specific examples include PEG 200, PEG 300, PEG 400, and PEG 600.

Among them, PEG 400 and PEG 600, are preferred.

The amount used of the low molecular weight polyethylene glycol ranges from 0.3 to 5% by weight based on the total weight of the transdermal preparation, and preferably ranging from 0.3 to 2% by weight, and more preferably 0.3 to 1% by weight based on the total weight of the transdermal preparation.

An amount used of the low molecular weight polyethylene glycol of less than 0.3% by weight is not preferable because such an amount interferes with the suppression of the crystallization of a non-steroidal anti-inflammatory drug, and an amount of more than 5% by weight is not preferable because such an amount increases the cohesiveness of the adhesive layer to interfere the processing into the patch.

Examples of the high molecular weight polyethylene glycol include a polyethylene glycol that is solid at an ordinary temperature (25° C.), such as polyethylene glycols having an average molecular weight of about 2,000 to 20,000, and specific examples include PEG 2000, PEG 4000, PEG 6000, and PEG 20000.

Among them, PEG 4000, PEG 6000 and PEG 20000, are preferred.

The amount used of the high molecular weight polyethylene glycol ranges from 1 to 10% by weight based on the total weight of the transdermal preparation, and preferably ranging from 1 to 7.5% by weight, and more preferably 4 to 6% by weight based on the total weight of the transdermal preparation.

An amount used of the high molecular weight polyethylene glycol of less than 1% by weight is not preferable because such an amount interferes with the suppression of the crystallization of a non-steroidal anti-inflammatory drug, and an amount of more than 10% by weight is not preferable because such an amount increases the cohesiveness of the adhesive layer to interfere with the processing into the patch.

Examples of the nonaqueous base material capable of being included in the transdermal preparation include a natural rubber, polyisoprene, a styrene-isoprene-styrene block copolymer (SIS), a styrene-butadiene-styrene block copolymer (SBS), a styrene-butadiene rubber, polyisobutylene, and a mixture of two or more of them.

The nonaqueous base material is preferably a mixture of two or more of them, and a mixture of a styrene-isoprene-styrene block copolymer (SIS) and polyisobutylene is preferred.

The amount used of the nonaqueous base material ranges from 10 to 40% by weight based on the total weight of the transdermal preparation and preferably ranging from 20 to 40% by weight based on the total weight of the transdermal preparation.

An amount used of the nonaqueous base material of less than 10% by weight is not preferable because such an amount leads to insufficient cohesiveness of the transdermal preparation by the addition of a tackifier and thus the adhesive layer remains on skin when the transdermal preparation is removed or because such an amount reduces shape retention properties and thus the adhesive layer sinks into the support. An amount of more than 40% by weight is not preferable because such an amount increases the cohesiveness of the adhesive layer to reduce workability and the adhesive power.

The mixture of styrene-isoprene-styrene block copolymer (SIS) and polyisobutylene which may be used as the nonaqueous base material will be further described.

Examples of the styrene-isoprene-styrene block copolymer (SIS) include a block copolymer containing 15 to 25% by weight of styrene (for example, JSR SIS 5229 (a styrene content of 15% by weight: manufactured by JSR Corporation), and JSR SIS 5002 (a styrene content of 22% by weight: manufactured by JSR Corporation)). In the present invention, these block copolymers may be used singly or as a mixture of two or more of them.

The amount used of the styrene-isoprene-styrene block copolymer (SIS) is 15% by weight or more and less than 30% by weight and preferably 17% by weight or more and less than 30% by weight, based on the total weight of the transdermal preparation.

Examples of the polyisobutylene include a polyisobutylene having various average molecular weights (for example, a molecular weight from 40,000 to 1,500,000). In the present invention, these polyisobutylenes may be used singly or as a mixture of two or more of them.

The amount used of the polyisobutylene ranges from 1 to 10% by weight and preferably ranging from 3 to 6% by weight, based on the total weight of the transdermal preparation.

When ibuprofen as a non-steroidal anti-inflammatory drug is used, examples of the preferable combinations of the low molecular weight polyethylene glycol, high molecular weight polyethylene glycol and nonaqueous base material are as follows:

(1) 5 to 8% by weight of ibuprofen, 0.3 to 2% by weight of a low molecular weight polyethylene glycol (PEG 600), 1 to 7.5% by weight of a high molecular weight polyethylene glycol (PEG 6000), 15 to 20% by weight of a styrene-isoprene-styrene block copolymer (SIS) (a styrene content of 15% by weight), and 3 to 6% by weight of polyisobutylene;

(2) 5 to 8% by weight of ibuprofen, 0.3 to 2% by weight of a low molecular weight polyethylene glycol (PEG 600), 1 to 7.5% by weight of a high molecular weight polyethylene glycol (PEG 20000), 15 to 20% by weight of a styrene-isoprene-styrene block copolymer (SIS) (a styrene content of 15% by weight), and 3 to 6% by weight of polyisobutylene;

(3) 5 to 8% by weight of ibuprofen, 0.3 to 2% by weight of a low molecular weight polyethylene glycol (PEG 400), 1 to 7.5% by weight of a high molecular weight polyethylene glycol (PEG 6000), 15 to 20% by weight of a styrene-isoprene-styrene block copolymer (SIS) (a styrene content of 15% by weight), and 3 to 6% by weight of polyisobutylene;

(4) 5 to 8% by weight of ibuprofen, 0.3 to 2% by weight of a low molecular weight polyethylene glycol (PEG 400), 1 to 7.5% by weight of a high molecular weight polyethylene glycol (PEG 20000), 15 to 20% by weight of a styrene-isoprene-styrene block copolymer (SIS) (a styrene content of 15% by weight), and 3 to 6% by weight of polyisobutylene;

(5) 5 to 8% by weight of ibuprofen, 0.3 to 2% by weight of a low molecular weight polyethylene glycol (PEG 600), 1 to 7.5% by weight of a high molecular weight polyethylene glycol (PEG 6000), 15 to 20% by weight of a styrene-isoprene-styrene block copolymer (SIS) (a styrene content of 22% by weight), and 3 to 6% by weight of polyisobutylene;

(6) 5 to 8% by weight of ibuprofen, 0.3 to 2% by weight of a low molecular weight polyethylene glycol (PEG 600), 1 to 7.5% by weight of a high molecular weight polyethylene glycol (PEG 20000), 15 to 20% by weight of a styrene-isoprene-styrene block copolymer (SIS) (a styrene content of 22% by weight), and 3 to 6% by weight of polyisobutylene;

(7) 5 to 8% by weight of ibuprofen, 0.3 to 2% by weight of a low molecular weight polyethylene glycol (PEG 400), 1 to 7.5% by weight of a high molecular weight polyethylene glycol (PEG 6000), 15 to 20% by weight of a styrene-isoprene-styrene block copolymer (SIS) (a styrene content of 22% by weight), and 3 to 6% by weight of polyisobutylene;

(8) 5 to 8% by weight of ibuprofen, 0.3 to 2% by weight of a low molecular weight polyethylene glycol (PEG 400), 1 to 7.5% by weight of a high molecular weight polyethylene glycol (PEG 20000), 15 to 20% by weight of a styrene-isoprene-styrene block copolymer (SIS) (a styrene content of 22% by weight), and 3 to 6% by weight of polyisobutylene;

(9) 5 to 8% by weight of ibuprofen, 0.3 to 2% by weight of a low molecular weight polyethylene glycol (PEG 400), 4 to 6% by weight of a high molecular weight polyethylene glycol (PEG 20000), 15 to 20% by weight of a styrene-isoprene-styrene block copolymer (SIS) (a styrene content of 15% by weight), and 3 to 6% by weight of polyisobutylene;

(10) 5 to 8% by weight of ibuprofen, 0.3 to 2% by weight of a low molecular weight polyethylene glycol (PEG 400), 4 to 6% by weight of a high molecular weight polyethylene glycol (PEG 20000), 15 to 20% by weight of a styrene-isoprene-styrene block copolymer (SIS) (a styrene content of 22% by weight), and 3 to 6% by weight of polyisobutylene;

(11) 5 to 7.5% by weight of ibuprofen, 0.3 to 1% by weight of a low molecular weight polyethylene glycol (PEG 400), 4 to 6% by weight of a high molecular weight polyethylene glycol (PEG 20000), 15 to 20% by weight of a styrene-isoprene-styrene block copolymer (SIS) (a styrene content of 15% by weight), and 5 to 6% by weight of polyisobutylene; and

(12) 5 to 7.5% by weight of ibuprofen, 0.3 to 1% by weight of a low molecular weight polyethylene glycol (PEG 400), 4 to 6% by weight of a high molecular weight polyethylene glycol (PEG 20000), 15 to 20% by weight of a styrene-isoprene-styrene block copolymer (SIS) (a styrene content of 22% by weight), and 5 to 6% by weight of polyisobutylene.

The transdermal preparation may further include a tackifier.

Examples of the tackifier usable in the transdermal preparation include, but are not particularly limited to, rosin derivatives (for example, rosin, a glycerin ester of rosin, hydrogenated rosin, a glycerin ester of hydrogenated rosin, and a pentaerythritol ester of rosin), aliphatic saturated hydrocarbon resins, aliphatic hydrocarbon resins, terpene resins, and maleic acid resins. A glycerin ester of hydrogenated rosin, an aliphatic hydrocarbon resin, and a terpene resin are preferred.

These tackifiers may be used singly or as a mixture of two or more of them.

The amount used of the tackifier ranges from 5 to 70% by weight, preferably ranging from 5 to 60% by weight, and more preferably ranging from 10 to 50% by weight, based on the total weight of the transdermal preparation.

An amount used of the tackifier of less than 5% by weight is likely to lead to insufficient improvement effect on the adhesive power of the transdermal preparation, which is provided by the addition of the tackifier, and an amount of more than 70% by weight is likely to increase skin irritation when the transdermal preparation is removed from skin.

The transdermal preparation may further include a plasticizer.

Examples of the plasticizer usable in the transdermal preparation include, but are not particularly limited to, petroleum oils (for example, a paraffinic process oil, a naphthenic process oil, and an aromatic process oil), squalane, squalene, plant oils (for example, an olive oil, a camellia oil, a castor oil, a tall oil, and a peanut oil), a silicon oil, dibasic acid esters (for example, dibutyl phthalate and dioctyl phthalate), liquid rubbers (for example, polybutene and a liquid isoprene rubber), liquid fatty acid esters (for example, isopropyl myristate, hexyl laurate, diethyl sebacate, and diisopropyl sebacate), diethylene glycol, glycol salicylate, propylene glycol, dipropylene glycol, triacetin, triethyl citrate, and crotamiton. Liquid paraffin, isopropyl myristate, diethyl sebacate, and hexyl laurate are preferred, and liquid paraffin is more preferred.

These plasticizers may be used singly or as a mixture of two or more of them.

The amount used of the plasticizer ranges from 5 to 70% by weight, preferably ranging from 10 to 60% by weight, and more preferably ranging from 10 to 50% by weight, based on the total weight of the transdermal preparation.

The transdermal preparation may further include L-menthol as a perfume or an absorption promoter.

The amount used of L-menthol ranges from 0.1 to 1% by weight and preferably ranging from 0.3 to 0.8% by weight, based on the total weight of the transdermal preparation.

The transdermal preparation may further include an absorption promoter in order to improve skin permeability of the drug.

For the absorption promoter usable in the transdermal preparation, any compound having skin absorption promotion effect can be used without limitation. Specific examples include $C_{6-20}$ fatty acids, fatty alcohols, fatty acid esters, fatty acid amides, fatty acid ethers, aromatic organic acids, aromatic alcohols, aromatic organic acid esters, and aromatic organic acid ethers.

These compounds may be saturated or unsaturated as well as straight, branched, or annular. Examples of the absorption promoter usable in the present invention further include lactic acid esters, acetic acid esters, monoterpene compounds, sesquiterpene compounds, azone, azone derivatives, glycerin fatty acid esters, propylene glycol fatty acid esters, sorbitan fatty acid esters (Spans™), polysorbate compounds (Tweens™), polyethylene glycol fatty acid esters, polyoxyethylene hydrogenated castor oil compounds (HCOs), polyoxyethylene alkyl ethers, sucrose fatty acid esters, and plant oils.

Among these absorption promoters, preferred are caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methyl laurate, hexyl laurate, lauric acid diethanolamide, isopropyl myristate, myristyl myristate, octyldodecyl myristate, cetyl palmitate, salicylic acid, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, 1-menthol, borneol, d-limonene, isoeugenol, isoborneol, nerol, dl-camphor, glycerin monocaprylate, glycerin monocaprate, glycerin monolaurate, glycerin monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, HCO-6.0, pyrothiodecane, and olive oil, and more preferred are lauryl alcohol, myristyl alcohol, isostearyl alcohol, lauric acid diethanolamide, glycerin monocaprylate, glycerin monocaprate, glycerin monooleate, sorbitan monolaurate, propylene glycol monolaurate, polyoxyethylene lauryl ether, and pyrothiodecane.

These absorption promoters may be used singly or as a mixture of two or more of them.

The amount used of the absorption promoter is not particularly limited, but ranges from 0.01 to 20% by weight, preferably ranging from 0.05 to 10% by weight, and more preferably ranging from 0.1 to 10% by weight, based on the total weight of the transdermal preparation.

An amount used of the absorption promoter of less than 0.01% by weight is likely to lead to insufficient improvement effect on skin permeability of the pharmaceutical drug, which is provided by the addition of the absorption promoter, and an amount of more than 20% by weight is likely to increase skin irritation such as edema and is likely to reduce the adhesiveness to skin.

The transdermal preparation may include additional ingredients to the compounds above, as necessary, for example an anti-oxidizing agent, a filler, a cross-linking agent, an antiseptic agent, an ultraviolet absorber. For the anti-oxidizing agent usable in the transdermal preparation, any anti-oxidizing agent can be used without limitation as long as it has been conventionally used for a patch. Specific examples of the preferably used anti-oxidizing agent are tocopherols and ester derivatives of them, ascorbic acid, ascorbyl stearate, nordihydroguaiaretic acid, dibutylhydroxytoluene (BHT), and butylhydroxyanisole.

For the filler usable in the transdermal preparation, any filler can be used without limitation as long as it has been conventionally used for a patch. Specific examples of the preferably used filler include calcium carbonate, magnesium carbonate, silicates (for example, aluminum silicate and magnesium silicate), silicic acid, barium sulfate, calcium sulfate, calcium zincate, zinc oxide, and titanium oxide.

For the cross-linking agent usable in the transdermal preparation, any cross-linking agent can be used without limitation as long as it has been conventionally used for a patch. Specific examples of the preferably used cross-linking agent include thermosetting resins such as an amino resin, a phenol resin, an epoxy resin, an alkyd resin, and an unsaturated polyester, isocyanate compounds, blocked isocyanate compounds, organic cross-linking agents, and inorganic cross-linking agents such as a metal and a metal compound.

For the antiseptic agent usable in the transdermal preparation, any antiseptic agent can be used without limitation as long as it has been conventionally used for a patch. Specific examples of the preferably used antiseptic agent include ethyl para-hydroxybenzoate, propyl para-hydroxybenzoate, and butyl para-hydroxybenzoate.

For the ultraviolet absorber usable in the transdermal preparation, any ultraviolet absorber can be used without limitation as long as it has been conventionally used for a patch. Specific examples of the preferably used ultraviolet absorber include p-aminobenzoic acid derivatives, anthranilic acid derivatives, salicylic acid derivatives, coumarin derivatives, amino acid compounds, imidazoline derivatives, pyrimidine derivatives, and dioxane derivatives.

Each amount used of the anti-oxidizing agent, the filler, the cross-linking agent, the antiseptic agent, and the ultraviolet absorber is not particularly limited, but the total amount used of the anti-oxidizing agent, the filler, the cross-linking agent, the antiseptic agent, and the ultraviolet absorber ranges from 0 to 10% by weight, preferably ranging from 0 to 5% by weight, and more preferably ranging from 0 to 2% by weight, based on the total weight of the transdermal preparation.

The support used in the patch containing a non-steroidal anti-inflammatory drug of the present invention is not particularly limited as long as it can support the adhesive layer, and an expandable support and a non-expandable support can be used.

Specific examples of such a support include cloth, non-woven fabric, polyurethane, polyester, polyvinyl acetate, polyvinylidene chloride, polyethylene, polyethylene terephthalate, an aluminum sheet, and a composite material of them.

The patch containing a non-steroidal anti-inflammatory drug of the present invention can be produced by, for example, a method of forming an adhesive layer by applying the transdermal preparation on the support.

The patch containing a non-steroidal anti-inflammatory drug of the present invention may be produced by covering the coated face (ointment face) of the adhesive layer that is formed on the support by the application, with a liner (covering article for the ointment face).

Examples of the preferably used liner include a vinyl chloride film, a polyethylene film, a polypropylene film, a polyester film, a polyethylene terephthalate separator according to the pharmaceutical additive specification, and a release paper (exfoliate paper).

The patch containing a non-steroidal anti-inflammatory drug may also be produced by a method of covering the coated face of the adhesive layer that is formed on the liner by the application, with the support.

The present invention will be further described with reference to the following examples. Further examples with the scope of the invention will be apparent to the person skilled in the art.

Examples 1 to 31 and Comparative Examples 1 to 5

In accordance with the contents described in the component table in Table 1, each component was mixed and stirred to prepare a transdermal preparation. The preparation was applied to a polyethylene terephthalate liner using a coater at a coating amount described in Table 1. The coated liner was covered with a polyethylene terephthalate film/knit lamination support to produce a patch for each of Examples 1 to 31 and Comparative Examples 1 to 5.

In Table, NSAID means a non-steroidal anti-inflammatory drug, and SIS means a styrene-isoprene-styrene block copolymer.

For SIS (15), JSR SIS 5229 (a styrene content of 15% by weight: manufactured by JSR Corporation) was used, for SIS (22), JSR SIS 5002 (a styrene content of 22% by weight: manufactured by JSR Corporation) was used, for the polyisobutylene, OPPANOL (registered trademark: manufactured by BASF) was used, and for the hydrogenated rosin glycerin ester, KE-311 (manufactured by Arakawa Chemical Industries, Ltd.) was used.

TABLE 1

Component Table

| | | Component (% by weight) | | | | | | | | | | | | | |
|---|---|---|---|---|---|---|---|---|---|---|---|---|---|---|---|
| | | Polyethylene glycol component | | | | | Nonaqueous base material | | | | | | | | |
| | | Low molecular weight | | High molecular weight | | | SIS | | Poly-iso- | Hydrogenated rosin | Liquid | L- | Dibutyl- | Hydrous | Total | Coating |
| Example number | NSAID Ibuprofen | PEG 600 | PEG 400 | PEG 20000 | PEG 6000 | PEG 4000 | SIS (15) | SIS (22) | butyl-ene | glycerin ester | paraffin | menthol | hydroxy-toluene | silicon dioxide | amount (% by weight) | amount (g/140 cm²) |
| Example 1 | 10 | — | 5 | 10 | — | — | 20 | — | 3 | 30 | 20.5 | 0.5 | 0.5 | 0.5 | 100 | 2.0 |
| Example 2 | 5 | — | 5 | 10 | — | — | 20 | — | 3 | 30 | 25.5 | 0.5 | 0.5 | 0.5 | 100 | 2.0 |
| Example 3 | 5 | — | 0.5 | 5 | — | — | 20 | — | 3 | 30 | 35 | 0.5 | 0.5 | 0.5 | 100 | 2.0 |
| Example 4 | 5 | — | 0.5 | 1 | — | — | 20 | — | 3 | 30 | 39 | 0.5 | 0.5 | 0.5 | 100 | 2.0 |
| Example 5 | 5 | — | 2 | 5 | — | — | 20 | — | 3 | 30 | 33.5 | 0.5 | 0.5 | 0.5 | 100 | 2.0 |
| Example 6 | 7.5 | — | 5 | 7.5 | — | — | 20 | — | 3 | 30 | 25.5 | 0.5 | 0.5 | 0.5 | 100 | 2.0 |
| Example 7 | 7.5 | — | 0.5 | 5 | — | — | 25 | — | 6 | 27.5 | 27 | 0.5 | 0.5 | 0.5 | 100 | 3.3 |
| Example 8 | 7.5 | — | 0.5 | 5 | — | — | 27.5 | — | 3 | 30 | 25 | 0.5 | 0.5 | 0.5 | 100 | 3.3 |
| Example 9 | 7.5 | — | 0.5 | 5 | — | — | — | 18 | 6 | 27.5 | 34 | 0.5 | 0.5 | 0.5 | 100 | 3.3 |
| Example 10 | 7.5 | — | 0.5 | 5 | — | — | — | 18 | 6 | 25 | 37 | 0.5 | — | 0.5 | 100 | 3.3 |
| Example 11 | 7.5 | 0.5 | — | 5 | — | — | — | 17 | 6 | 25 | 38 | 0.5 | 0.5 | — | 100 | 2.0 |
| Example 12 | 10 | — | 5 | — | 10 | — | 20 | — | 3 | 30 | 20.5 | 0.5 | 0.5 | 0.5 | 100 | 2.0 |
| Example 13 | 10 | — | 2.5 | — | 2.5 | — | 20 | — | 3 | 30 | 30.5 | 0.5 | 0.5 | 0.5 | 100 | 2.0 |
| Example 14 | 5 | — | 2.5 | — | 5 | — | 20 | — | 3 | 30 | 33 | 0.5 | 0.5 | 0.5 | 100 | 2.0 |
| Example 15 | 5 | — | 5 | — | 10 | — | 20 | — | 3 | 30 | 25.5 | 0.5 | 0.5 | 0.5 | 100 | 2.0 |
| Example 16 | 10 | — | 5 | — | 10 | — | 20 | — | 3 | 30 | 20.5 | 0.5 | 0.5 | 0.5 | 100 | 2.5 |
| Example 17 | 5 | — | 5 | — | — | 5 | 20 | — | 3. | 30 | 30.5 | 0.5 | 0.5 | 0.5 | 100 | 2.0 |

TABLE 1-continued

Component Table

| | | Polyethylene glycol component | | | | | Nonaqueous base material | | | | | | | | |
|---|---|---|---|---|---|---|---|---|---|---|---|---|---|---|---|
| | NSAID | Low molecular weight | | High molecular weight | | | SIS | | Poly-iso-butyl-ene | Hydro-genated rosin glycerin ester | Liquid paraf-fin | L-men-thol | Dibutyl-hydroxy-toluene | Hydrous silicon dioxide | Total amount (% by weight) | Coating amount (g/140 cm$^2$) |
| Example number | Ibu-pro-fen | PEG 600 | PEG 400 | PEG 20000 | PEG 6000 | PEG 4000 | SIS (15) | SIS (22) | | | | | | | | |
| Example 18 | 5 | — | 5 | — | — | 10 | 20 | — | 3 | 30 | 25.5 | 0.5 | 0.5 | 0.5 | 100 | 2.0 |
| Example 19 | 5 | — | 0.5 | 5 | — | — | — | 17 | 6 | 25 | 40.5 | 0.5 | 0.5 | — | 100 | 3.3 |
| Example 20 | 5 | — | 1.0 | 5 | — | — | — | 17 | 6 | 25 | 40.0 | 0.5 | 0.5 | — | 100 | 3.3 |
| Example 21 | 5 | — | 2.0 | 5 | — | — | — | 17 | 6 | 25 | 39.0 | 0.5 | 0.5 | — | 100 | 3.3 |
| Example 22 | 5 | — | 0.5 | 7.5 | — | — | — | 17 | 6 | 25 | 38.0 | 0.5 | 0.5 | — | 100 | 3.3 |
| Example 23 | 5 | — | 1.0 | 7.5 | — | — | — | 17 | 6 | 25 | 37.5 | 0.5 | 0.5 | — | 100 | 3.3 |
| Example 24 | 5 | — | 2.0 | 7.5 | — | — | — | 17 | 6 | 25 | 36.5 | 0.5 | 0.5 | — | 100 | 3.3 |
| Example 25 | 7.5 | — | 0.5 | 5 | — | — | — | 17 | 6 | 25 | 38.0 | 0.5 | 0.5 | — | 100 | 3.3 |
| Example 26 | 7.5 | — | 1.0 | 5 | — | — | — | 17 | 6 | 25 | 37.5 | 0.5 | 0.5 | — | 100 | 3.3 |
| Example 27 | 7.5 | — | 2.0 | 5 | — | — | — | 17 | 6 | 25 | 36.5 | 0.5 | 0.5 | — | 100 | 3.3 |
| Example 28 | 7.5 | — | 0.5 | 7.5 | — | — | — | 17 | 6 | 25 | 35.5 | 0.5 | 0.5 | — | 100 | 3.3 |
| Example 29 | 7.5 | — | 1.0 | 7.5 | — | — | — | 17 | 6 | 25 | 35.0 | 0.5 | 0.5 | — | 100 | 3.3 |
| Example 30 | 7.5 | — | 2.0 | 7.5 | — | — | — | 17 | 6 | 25 | 34.0 | 0.5 | 0.5 | — | 100 | 3.3 |
| Example 31 | 7.5 | — | 0.3 | 5 | — | — | — | 18 | 6 | 25 | 36.7 | 0.5 | 0.5 | 0.5 | 100 | 3.3 |
| Com. Ex. 1 | 5 | — | — | 10 | — | — | 20 | — | 3 | 30 | 30.5 | 0.5 | 0.5 | 0.5 | 100 | 2.0 |
| Com. Ex. 2 | 5 | — | — | 5 | — | — | 20 | — | 3 | 30 | 35.5 | 0.5 | 0.5 | 0.5 | 100 | 2.0 |
| Com. Ex. 3 | 10 | — | 2 | — | — | — | 20 | — | 3 | 15 | 48.5 | 0.5 | 0.5 | 0.5 | 100 | 2.0 |
| Com. Ex. 4 | 10 | — | — | — | — | — | 20 | — | 5 | 40 | 23.5 | 0.5 | 0.5 | 0.5 | 100 | 2.0 |
| Com. Ex. 5 | 7.5 | — | 0.2 | 5 | — | — | — | 18 | 6 | 25 | 36.7 | 0.5 | 0.5 | 0.5 | 100 | 3.3 |

Test Example 1

In Vitro Skin Permeation Test Using Excised Rat Abdomen Skin

An abdomen skin of a hairless rat (HWY/S1c, male, 7 weeks old) was excised and fixed in a vertical diffusion cell (Franz cell) with the dermis layer down. Each patch of Examples 1, 3, 5, 12, 14, 15, 16, 18, 19 and 25 to 30 that was cut into a circular shape having a diameter of 1 cm was applied onto the horny layer after the liner was removed. To the dermis layer side, a receiver solution (pH 7.4 phosphate buffer) was poured, and stirred by the circulation of water at 32° C. The receiver solution was sequentially collected, and the amount of the drug contained was determined with HPLC. Table 2 shows the 24-hour accumulated permeation amount calculated from the determined results in the patch of each Example.

TABLE 2

In Vitro Skin Permeability Test Result

| Example number | 24-hour accumulated permeation amount (μg/cm$^2$) |
|---|---|
| Example 1 | 544 |
| Example 3 | 460 |
| Example 5 | 383 |
| Example 12 | 477 |
| Example 14 | 564 |
| Example 15 | 340 |
| Example 16 | 627 |
| Example 18 | 369 |
| Example 19 | 392.5 |
| Example 25 | 525.9 |
| Example 26 | 388.4 |
| Example 27 | 328.1 |
| Example 28 | 315.3 |
| Example 29 | 381.5 |
| Example 30 | 401.2 |

Results:
Each patch showed a permeation amount of more than about 300 μg/cm² for 24 hours. The same test on a commercially available patch containing ibuprofen (ibugel) revealed a 24-hour accumulated permeation amount of 300 to 400 μg/mL. Therefore, it was found that the patch of the present invention had a permeability equivalent or more than that of the commercially available patch containing ibuprofen.

Test Example 2

Confirmation of Crystallization and Sublimation

Each patch of Examples 1 to 31 and Comparative Examples 1 to 5 was independently sealed in a composite aluminum package bag and stored at room temperature for 4 weeks. Then, the inside and outside of the package bag and the patch were visually observed to confirm the presence or absence of crystal precipitation and sublimation.
The results are shown in Table 3.

TABLE 3

Confirmation of Crystallization and Sublimation

| Example number | Presence or absence of crystal precipitation and sublimation |
|---|---|
| Example 1 | Absent |
| Example 2 | Absent |
| Example 3 | Absent |
| Example 4 | Absent |
| Example 5 | Absent |
| Example 6 | Absent |
| Example 7 | Absent |
| Example 8 | Absent |
| Example 9 | Absent |
| Example 10 | Absent |
| Example 11 | Absent |
| Example 12 | Absent |
| Example 13 | Absent |
| Example 14 | Absent |
| Example 15 | Absent |
| Example 16 | Absent |
| Example 17 | Absent |
| Example 18 | Absent |
| Example 19 | Absent |
| Example 20 | Absent |
| Example 21 | Absent |
| Example 22 | Absent |
| Example 23 | Absent |
| Example 24 | Absent |
| Example 25 | Absent |
| Example 26 | Absent |
| Example 27 | Absent |
| Example 28 | Absent |
| Example 29 | Absent |
| Example 30 | Absent |
| Example 31 | Absent |
| Comparative Example 1 | Present |
| Comparative Example 2 | Present |
| Comparative Example 3 | Present |
| Comparative Example 4 | Present |
| Comparative Example 5 | Present |

Results:
In the patches of Comparative Examples 1 and 2 that contained the high molecular weight polyethylene glycol alone as the polyethylene glycol component, the patch of Comparative Example 3 that contained the low molecular weight polyethylene glycol alone, the patch of Comparative Example 4 that contained no polyethylene glycol component, and the patch of Comparative Example 5 that contained the low molecular weight polyethylene glycol in only 0.2% by weight being less than 0.3 to 5% by weight, the crystal was confirmed in the transdermal preparation, on the liner surface, or on the inner surface of the package material. In contrast, in each patch of Examples 1 to 31 that used a combination of the low molecular weight and high molecular weight polyethylene glycols as the polyethylene glycol component, and that contained the low molecular weight polyethylene glycol in an amount of 0.3 to 5% by weight and the high molecular weight polyethylene glycol in an amount of 1 to 10% by weight, such crystal precipitation and sublimation were not confirmed.

Test Example 3

Stability Test

Each patch of Examples 3, 5, 10, 11 and 19 to 30 was stored at 40° C. for predetermined period, and the drug content (ibuprofen) and the amount of decomposition product were measured in the transdermal preparation.
Results are shown in Table 4.

TABLE 4

Drug Content and Amount of Decomposition Product after Storage at 40° C.

| Example number | Period of preservation | Ratio with respect to start (%) | Decomposition product (%) |
|---|---|---|---|
| Example 3 | 3 months | 98.6 | 0.66 |
| Example 5 | 3 months | 98.6 | 1.79 |
| Example 10 | 6 months | 97.9 | 0.95 |
| Example 11 | 6 months | 97.7 | 0.77 |
| Example 19 | 2 months | 99.9 | 0.40 |
| Example 20 | 2 months | 98.8 | 0.72 |
| Example 21 | 2 months | 98.0 | 1.31 |
| Example 22 | 2 months | 100.3 | 0.32 |
| Example 23 | 2 months | 99.7 | 0.59 |
| Example 24 | 2 months | 98.9 | 1.05 |
| Example 25 | 2 months | 98.1 | 0.39 |
| Example 26 | 2 months | 98.2 | 0.74 |
| Example 27 | 2 months | 97.3 | 1.55 |
| Example 28 | 2 months | 98.9 | 0.34 |
| Example 29 | 2 months | 98.8 | 0.72 |
| Example 30 | 2 months | 98.1 | 1.29 |

Results:
Each drug content (ibuprofen) in the transdermal preparation after the storage at 40° C. was maintained at a ratio of 97% or more with respect to that at the start. Therefore, it was revealed that the transdermal preparation in the patch of the present invention had good stability.

Test Example 4

Industrial Adaptability Test

The patch of Example 2 and the patches of Examples 32 and 33 that were different from the patch of Example 2 in the content of the high molecular weight polyethylene glycol, the patch of Example 15 and the patches of Examples 34 and 35 that were different from the patch of Example 15 in the content of the high molecular weight polyethylene glycol, and the patches of Examples 17 and 18 and the patch of Example 36 that was different from the patches of Examples 17 and 18 in the content of the high molecular weight polyethylene glycol were subjected to the evaluation of industrial adaptability.
The content of components of each patch is shown in Table 5.

TABLE 5

| | | Component (% by weight) | | | | | | | | | | | | | | |
|---|---|---|---|---|---|---|---|---|---|---|---|---|---|---|---|---|
| | | Polyethylene glycol component | | | | | Nonaqueous base material | | | | | | | | | Amount |
| | | Low molecular weight | | High molecular weight | | | SIS | | Poly-iso- | Hydro-genated rosin | Liquid | L- | Dibutyl- | Hydrous | Total | of coating |
| Example number | NSAID Ibu-pro-fen | PEG 600 | PEG 400 | PEG 20000 | PEG 6000 | PEG 4000 | SIS (15) | SIS (22) | butyl-ene | glycerin ester | paraf-fin | men-thol | hydroxy-toluene | silicon dioxide | amount (% by weight) | (g/140 cm²) |
| Example 2 | 5 | — | 5 | 10 | — | — | 20 | — | 3 | 30 | 25.5 | 0.5 | 0.5 | 0.5 | 100 | 2.0 |
| Example 32 | 5 | — | 5 | 7.5 | — | — | 20 | — | 3 | 30 | 28.0 | 0.5 | 0.5 | 0.5 | 100 | 2.0 |
| Example 33 | 5 | — | 5 | 5 | — | — | 20 | — | 3 | 30 | 30.5 | 0.5 | 0.5 | 0.5 | 100 | 2.0 |
| Example 15 | 5 | — | 5 | — | 10 | — | 20 | — | 3 | 30 | 25.5 | 0.5 | 0.5 | 0.5 | 100 | 2.0 |
| Example 24 | 5 | — | 5 | — | 7.5 | — | 20 | — | 3 | 30 | 28.0 | 0.5 | 0.5 | 0.5 | 100 | 2.0 |
| Example 35 | 5 | — | 5 | — | 5 | — | 20 | — | 3 | 30 | 30.5 | 0.5 | 0.5 | 0.5 | 100 | 2.0 |
| Example 18 | 5 | — | 5 | — | — | 10 | 20 | — | 3 | 30 | 25.5 | 0.5 | 0.5 | 0.5 | 100 | 2.0 |
| Example 36 | 5 | — | 5 | — | — | 7.5 | 20 | — | 3 | 30 | 28.0 | 0.5 | 0.5 | 0.5 | 100 | 2.0 |
| Example 17 | 5 | — | 5 | — | — | 5 | 20 | — | 3 | 30 | 30.5 | 0.5 | 0.5 | 0.5 | 100 | 2.0 |

The evaluation of industrial adaptability was made by evaluating kneading performance, transfer performance and ointment spreading performance according to the evaluation method and evaluation criteria shown in Table 6. In the meantime, the lowest evaluation among the kneading performance, transfer performance and ointment spreading performance was adopted as the evaluation of industrial adaptability of the patch.

TABLE 6

Evaluation Method and Evaluation Criteria of Industrial Adaptability

| Item | | Evaluation Method | Evaluation Criteria |
|---|---|---|---|
| Industrial Adaptability | Kneading Performance | Agitation property in kneading ointment is evaluated. | A: Good. B: It was possible to agitate. C: It was possible to agitate but not preferable. D: No good. |
| | Transfer Performance | Transfer property of kneaded ointment to an ointment spreader is evaluated. | A: Good. B: It was possible to transfer. C: It was possible to transfer but not preferable. D: No good. |
| | Ointment Spreading Performance | Spreading property is evaluated. | A: Good. B: It was possible to spread. C: It was possible to spread but not preferable. D: No good. |

The results of evaluation of industrial adaptability are shown in Table 7 together with the 24-hour accumulated permeation amount (only Examples 2, 15 and 18) and the presence or absence of crystal precipitation and sublimation.

TABLE 7

| Example number | 24-hour accumulated permeation amount (µg/cm²) | Presence or absence of crystal precipitation and sublimation | Industrial adaptability |
|---|---|---|---|
| Example 2 | 294 | Absent | C |
| Example 32 | | Absent | B |
| Example 33 | | Absent | A |
| Example 15 | 340 | Absent | C |
| Example 34 | | Absent | B |
| Example 35 | | Absent | A |
| Example 18 | 369 | Absent | C |
| Example 36 | | Absent | B |
| Example 17 | | Absent | A |

Results:

It turned out that any of the patches of Examples 2, 15 and 18 containing 10% by weight of a high molecular weight polyethylene glycol showed good 24-hour accumulated permeation property, and no crystal precipitation or sublimation, but those patches showed a little low industrial adaptability.

On the other hand, the patches containing the high molecular weight polyethylene glycol in an amount of 7.5% by weight less than that of Examples 2, 15 and 18 were improved in industrial adaptability (Examples 32, 34 and 36), and the patches containing the high molecular weight polyethylene glycol in an amount of 5% by weight further less than that of Examples 32, 34 and 36 were further improved in industrial adaptability (Examples 33, 35 and 17).

The invention claimed is:
1. A patch including an adhesive layer comprising a transdermal preparation on a support, the transdermal preparation comprising:
10 to 40% by weight of a nonaqueous base material based on the total weight of the transdermal preparation,
1 to 10% by weight of a non-steroidal anti-inflammatory drug based on the total weight of the transdermal preparation, and a polyethylene glycol component comprising:
- 0.3 to 5% by weight of a low molecular weight polyethylene glycol based on the total weight of the transdermal preparation, and
- 1 to 10% by weight of a high molecular weight polyethylene glycol based on the total weight of the transdermal preparation.

2. The patch according to claim 1, in which the content of the low molecular weight polyethylene glycol is 0.3 to 2% by weight based on the total weight of the transdermal preparation.

3. The patch according to claim 1, in which the non-steroidal anti-inflammatory drug is selected from a group consisting of ibuprofen, ketoprofen, flurbiprofen, diclofenac, and naproxen.

4. The patch according to claim 3, in which the non-steroidal anti-inflammatory drug is selected from a group consisting of ibuprofen, ketoprofen, and naproxen.

5. The patch according to claim 4, in which the non-steroidal anti-inflammatory drug is ibuprofen.

6. The patch according to claim 5, in which the content of the ibuprofen is 2.5 to 10% by weight based on the total weight of the transdermal preparation.

7. The patch according to claim 1, in which the nonaqueous base material comprises a styrene-isoprene-styrene block copolymer (SIS) and polyisobutylene.

8. The patch according to claim 5, in which the content of the ibuprofen is 5 to 10% by weight based on the total weight of the transdermal preparation.

9. The patch according to claim 1, in which the polyethylene glycol component comprises 0.3 to 2% by weight of a low molecular weight polyethylene glycol based on the total weight of the transdermal preparation.

10. The patch according to claim 1, in which the polyethylene glycol component comprises 1 to 7.5% by weight of a high molecular weight polyethylene glycol based on the total weight of the transdermal preparation.

11. The patch according to claim 1, in which the nonaqueous base material is 20 to 40% by weight based on the total weight of the transdermal preparation.

12. The patch according to claim 5, in which the polyethylene glycol component comprises 0.3 to 2% by weight of a low molecular weight polyethylene glycol based on the total weight of the transdermal preparation.

13. The patch according to claim 5, in which the polyethylene glycol component comprises 1 to 7.5% by weight of a high molecular weight polyethylene glycol based on the total weight of the transdermal preparation.

14. The patch according to claim 5, in which the nonaqueous base material is 20 to 40% by weight based on the total weight of the transdermal preparation.

15. The patch according to claim 1, wherein
the non-steroidal anti-inflammatory drug is ibuprofen and is 5 to 8% by weight based on the total weight of the transdermal preparation, and
the polyethylene glycol component comprises 0.3 to 2% by weight of a low molecular weight polyethylene glycol based on the total weight of the transdermal preparation and 1 to 7.5% by weight of a high molecular weight polyethylene glycol based on the total weight of the transdermal preparation.

16. The patch according to claim 1, wherein
the non-steroidal anti-inflammatory drug is ibuprofen and is 5 to 8% by weight based on the total weight of the transdermal preparation, and
the polyethylene glycol component comprises 0.3 to 2% by weight of a low molecular weight polyethylene glycol based on the total weight of the transdermal preparation and 4 to 6% by weight of a high molecular weight polyethylene glycol based on the total weight of the transdermal preparation.

17. The patch according to claim 1, wherein
the non-steroidal anti-inflammatory drug is ibuprofen and is 5 to 7.5% by weight based on the total weight of the transdermal preparation, and
the polyethylene glycol component comprises 0.3 to 1% by weight of a low molecular weight polyethylene glycol based on the total weight of the transdermal preparation and 4 to 6% by weight of a high molecular weight polyethylene glycol based on the total weight of the transdermal preparation.

18. The patch according to claim 7, wherein
the non-steroidal anti-inflammatory drug is ibuprofen and is 5 to 8% by weight based on the total weight of the transdermal preparation,
the polyethylene glycol component comprises 0.3 to 2% by weight of a low molecular weight polyethylene glycol based on the total weight of the transdermal preparation and 1 to 7.5% by weight of a high molecular weight polyethylene glycol based on the total weight of the transdermal preparation,
the styrene-isoprene-styrene block copolymer (SIS) is 15 to 20% by weight based on the total weight of the transdermal preparation, and
the polyisobutylene is 3 to 6% by weight based on the total weight of the transdermal preparation.

19. The patch according to claim 7, wherein
the non-steroidal anti-inflammatory drug is ibuprofen and is 5 to 8% by weight based on the total weight of the transdermal preparation,
the polyethylene glycol component comprises 0.3 to 2% by weight of a low molecular weight polyethylene glycol based on the total weight of the transdermal preparation and 4 to 6% by weight of a high molecular weight polyethylene glycol based on the total weight of the transdermal preparation,
the styrene-isoprene-styrene block copolymer (SIS) is 15 to 20% by weight based on the total weight of the transdermal preparation, and
the polyisobutylene is 3 to 6% by weight based on the total weight of the transdermal preparation.

20. The patch according to claim 7, wherein
the non-steroidal anti-inflammatory drug is ibuprofen and is 5 to 7.5% by weight based on the total weight of the transdermal preparation,
the polyethylene glycol component comprises 0.3 to 1% by weight of a low molecular weight polyethylene glycol based on the total weight of the transdermal preparation and 4 to 6% by weight of a high molecular weight polyethylene glycol based on the total weight of the transdermal preparation,
the styrene-isoprene-styrene block copolymer (SIS) is 15 to 20% by weight based on the total weight of the transdermal preparation, and
the polyisobutylene is 5 to 6% by weight based on the total weight of the transdermal preparation.

* * * * *